United States Patent [19]
Hillman et al.

[11] Patent Number: 5,869,291
[45] Date of Patent: Feb. 9, 1999

[54] RAB PROTEINS

[75] Inventors: Jennifer L. Hillman, San Jose; Surya K. Goli, Sunnyvale; Olga Bandman, Mountain View, all of Calif.

[73] Assignee: Incyte Pharmaceuticals, Inc., Palo Alto, Calif.

[21] Appl. No.: 773,423

[22] Filed: Dec. 27, 1996

[51] Int. Cl.$^6$ .............................. C07H 21/04; C12Q 1/68; C12N 15/63; C12N 1/20
[52] U.S. Cl. ..................... 435/69.1; 536/24.31; 536/23.1; 536/23.5; 435/6; 435/252.3; 435/320.1
[58] Field of Search .............................. 536/23.1, 24.31; 435/6, 252.3, 320.1, 69.1

[56] References Cited

PUBLICATIONS

Burgess et al. J. Cell Biol. 11:2129–2138, 1990.
Lazar et al. Mol. Cell. Biol. 8: 1247–1252, 1988.
Tao et al. J. Immunol. 143(8): 2595–2601, 1989.
Gillies et al. Human Antibod. & Hybridomas 1(1): 47–54, 1990.
Joost, HG. GeneBank. Accession No. X78606, 1984.
Schmidt, A. Mol. Cell Biol. 6: 347–354, 1986.
Ueno, H. GeneBank. Accession No. D38516, 1994.
Lai et al. Genomics 22(3): 610–616, 1994.
Hillier, et al. GeneBank, Accession Nos. W71996, H98534, 1995.
Lombardi, D. et al. Embo J. 12: 677–682, 1995.
Ioannou, YA et al. GeneBank. Accession Nos. P51151, W44103, 1996.
Khosravi–Far, R., et al., "Isoprenoid modification of rab proteins terminating in CC or CXC motifs," *Proc. Natl. Acad. Sci. USA,* 88:6264–6268 (1991).
Seabra, M., et al., "Deficient Geranylgeranylation of Ram/Rab27 in Choroideremia," *The Journal of Biological Chemistry,* 270(41):24420–24427 (1995).
Seabra, M., et al., "Retinal Degeneration in Choroideremia: Deficiency ofRab Geranylgeranyl Transferase," *Science,* 259:377–381 (1993).
Zahraoui, A., et al., "The Human Rab Genes Encode a Family of GTP–binding Proteins Related to Yeast YPT1 and SEC4 Products Involved in Secretion," *The Journal of Biological Chemistry,* 264(21):12394–12401 (1989).

Chen, D., et al., "Molecular cloning of two novel rab genes from human melanocytes," *Gene,* 174:129–134 (1996).
Fridell, R., et al., "Nuclear export of late HIV–1 mRNAs occurs via a cellular protein export pathway," *Proc. Natl. Acad. Sci. USA,* 93:4421–4424 (1996).
Tuomikoski, T., et al., "Inhibition of endocytic vesicle fusion in vitro, by the cell–cycle control protein kinase cdc2," *Nature,* 342:942–945 (1989).
Brauers, A., et al., "Alternative mRNA splicing of the novel GTPase Rab28 generates isoforms with different C–termini," *Eur. J. Biochem.,* 237:833–840 (1996).
Goldenring, J., et al., "Identification of a Small GTP–binding Protein, Rab25, Expressed in the Gastrointestinal Mucosa, Kidney, and Lung," *The Journal of Biological Chemistry,* 268(25):18419–18422 (1993).
Obavier, et al., P., "Molecular Cloning of YPT1/SEC4–Related cDNAs from an Epithelial Cell Line," *Molecular and Cellular Biology,* 10(12):6578–6585 (1990).
Davies, J., et al., "Cloning and Mapping of Human RAB7 and Rab9 cDNA Sequences and Identification of a Rab9 Pseudogene," *Genomics,* 41:131–134 (1997).

*Primary Examiner*—Lila Feisee
*Assistant Examiner*—Geetha P. Bansal
*Attorney, Agent, or Firm*—Leanne C. Price; Lucy J. Billings; Incyte Pharmaceuticals, Inc.

[57] ABSTRACT

The present invention provides three Rab proteins (designated individually as HRABS-1, HRABS-2, and HRABS-3, and collectively as HRABS) and polynucleotides which identify and encode HRABS. The invention also provides genetically engineered expression vectors and host cells comprising the nucleic acid sequences encoding HRABS and a method for producing HRABS. The invention also provides for use of HRABS and agonists, antibodies, or antagonists specifically binding HRABS, in the prevention and treatment of diseases associated with expression of HRABS. Additionally, the invention provides for the use of antisense molecules to polynucleotides encoding HRABS for the treatment of diseases associated with the expression of HRABS. The invention also provides diagnostic assays which utilize the polynucleotide, or fragments or the complement thereof, and antibodies specifically binding HRABS.

18 Claims, 11 Drawing Sheets

```
            10                  19                  28                  37                  46              55
5' TGG CGC TTG CCG AGT GAT TCT CCT CGA ATA CCT CCT GCC GGC GCG GAG ACA CCG 64                  73                  82                  91                 100             109
   GGG CGG GGG TCC TGC CGC AAC TAC CTC CCT TCC TCC TCT CCC CCG CCC CCG GAG 118                 127                 136                 145                 154             163
   CCT TCA TCC TTC CCT TCC CCC CCC ACC TCG AGG GGC GGG CCT GGT TCC CGG GAC 172                 181                 190                 199                 208             217
   ACC ATG TCG GAC TCT GAG GAG GAG AGC CAG GAC CGG CAA CTG AAA ATC GTC GTG
        M   S   D   S   E   E   E   S   Q   D   R   Q   L   K   I   V   V 226                 235                 244                 253                 262             271
   CTG GGG GAC GNN GCC TCC GGG AAG ACC TCC TTA ACT ACG TGT TTT GCT CAA GAA
   L   G   D   X   A   S   G   K   T   S   L   T   T   C   F   A   Q   E 280                 289                 298                 307                 316             325
   ACT TTT GGG AAA CAG TAC AAA CAA ACT ATA GGA CTG GAT TTC TTT TTG AGA AGG
   T   F   G   K   Q   Y   K   Q   T   I   G   L   D   F   F   L   R   R 334                 343                 352                 361                 370             379
   ATA ACA TTG CCA GGA AAC TTG AAT GTT ACC CTT CAA ATT TGG GAT ATA GGA GGG
   I   T   L   P   G   N   L   N   V   T   L   Q   I   W   D   I   G   G 388                 397                 406                 415                 424             433
   CAG ACA ATA GGA GGC AAA ATG TTG GAT AAA TAT ATC TAT GGA GCA CAG GGA GTC
   Q   T   I   G   G   K   M   L   D   K   Y   I   Y   G   A   Q   G   V 442                 451                 460                 469                 478             487
   CTC TTG GTA TAT GAT ATT ACA AAT TAT CAA AGC TTT GAG AAT TTA GAA GAT TGG
   L   L   V   Y   D   I   T   N   Y   Q   S   F   E   N   L   E   D   W 496                 505                 514                 523                 532             541
   TAT ACT GTG GTG AAG AAA GTG AGC NAG GAG TCA GAA ACT CAG CCA CTG GTT GCC
   Y   T   V   V   K   K   V   S   X   E   S   E   T   Q   P   L   V   A 550                 559                 568                 577                 586             595
   TTG GTA GGC AAT AAA ATT GAT TTG GAG CAT ATG CGA ACA ATA AAA CCT GAA AAA
   L   V   G   N   K   I   D   L   E   H   M   R   T   I   K   P   E   K 604                 613                 622                 631                 640             649
   CAC TTA CGG TTT TGC CAG GAA AAT GGT TTT AGT AGC CAC TTT GTC TCA GCC AAG
   H   L   R   F   C   Q   E   N   G   F   S   S   H   F   V   S   A   K 658                 667                 676                 685                 694             703
   ACA GGA GAC TCT GTC TTC CTG TGC TTT CAG AAA GTT GCT GCT GAA ATC CTT GGG
   T   G   D   S   V   F   L   C   F   Q   K   V   A   A   E   I   L   G
```

FIGURE 1A

```
         712         721         730         739         748         757
ATC AAA TTA AAC AAN NAG CAG AAW TRG MAC AGT CAC AGW GGG GTG GTG AAG GSA
 I   K   L   N   X   X   Q   X   X   X   S   H   X   G   V   V   K   X 766         775         784         793         802         811
GRT ATT GTA AAC TAC AAC CAG GAA CCT ATG TCA AGG ACT KTT AAC CCT CCT AGA
 X   I   V   N   Y   N   Q   E   P   M   S   R   T   X   N   P   P   R 820         829         838         847         856         865
AGC TCT ATG TGT GCA GTT CAG TGA GCG CAT TTT NCT TTT GTN TTG ATA GTT CTG
 S   S   M   C   A   V   Q 874         883         892         901         910
GCT GCC CTT CAA CTC TGG GTG GGN CCC NAG GGC TTC TAG GAC TTG TTT T 3'
```

FIGURE 1B

```
                10              19              28              37              46              55
5' GCA TTG AGC CAA CAC ACA GAT TTG TCG CCT CTG TCC CCG AAG ACA CCT GCA CCC 64              73              82              91              100             109
   TCC ATG CGG ANC AAG ATG GGG AAT GGA ACT GAG GAA GAT TAT AAC TTT GTC TTC
       M   R   X   K   M   G   N   G   T   E   E   D   Y   N   F   V   F 118             127             136             145             154             163
   AAG GTG GTG CTG ATC GGC GAA TCA GGT GTG GGG AAG ACC AAT CTA CTC TCC CGA
   K   V   V   L   I   G   E   S   G   V   G   K   T   N   L   L   S   R 172             181             190             199             208             217
   TTC ACG CGC AAT GAG TTC AGC CAC GAC AGC CGC ACC ACC ATC GGG GTT GAG TTC
   F   T   R   N   E   F   S   H   D   S   R   T   T   I   G   V   E   F 226             235             244             253             262             271
   TCC ACC CGC ACT GTG ATG TTG GGC ACC GCT GCT GTC AAG GCT CAG ATC TGG GAC
   S   T   R   T   V   M   L   G   T   A   A   V   K   A   Q   I   W   D 280             289             298             307             316             325
   ACA GCT GGC CTG GAG CGG TAC CGA GCC ATC ACC TCG GCG TAC TAT CGT GGT GCA
   T   A   G   L   E   R   Y   R   A   I   T   S   A   Y   Y   R   G   A 334             343             352             361             370             379
   GTG GGG GCC CTC CTG GTG TTT GAC CTA ACC AAG CAC CAG ACC TAT GCT GTG GTG
   V   G   A   L   L   V   F   D   L   T   K   H   Q   T   Y   A   V   V 388             397             406             415             424             433
   GAG CGA TGG CTG AAG GAG CTC TAT GAC CAT GCT GAA GCC ACG ATC GTC GTC ATG
   E   R   W   L   K   E   L   Y   D   H   A   E   A   T   I   V   V   M 442             451             460             469             478             487
   CTC GTG GGT AAC AAA AGT GAC CTC AGC CAG GGC CGG GAA GTG CCC ACT GAG GAG
   L   V   G   N   K   S   D   L   S   Q   G   R   E   V   P   T   E   E 496             505             514             523             532             541
   GCC CGA ATG TTC GCT GAA AAC AAT GGA CTG CTC TTC CTG GAG ACC TCA GCC CTG
   A   R   M   F   A   E   N   N   G   L   L   F   L   E   T   S   A   L 550             559             568             577             586             595
   GAC TCT ACC AAT GTT GAG CTA GCC TTT GAG ACT GTC CTG AAA GAA ATC TTT GCG
   D   S   T   N   V   E   L   A   F   E   T   V   L   K   E   I   F   A 604             613             622             631             640             649
   AAG GTG TCC AAG CAG AGA CAG AAC AGC ATC CGG ACC AAT GCC ATC ACT CTG GGC
   K   V   S   K   Q   R   Q   N   S   I   R   T   N   A   I   T   L   G 658             667             676             685             694             703
   AGT GCC CAG GNT GGA CAG GAG CCT GGC CCT GGG GAG AAG AGG GCC TGT TGC ATC
   S   A   Q   X   G   Q   E   P   G   P   G   E   K   R   A   C   C   I
```

FIGURE 2A

```
        712         721         730         739         748         757
AGC CTC TGA CCT TGG CCA GCA CCA CCT GCC CCC ACT GGC TTT TTG GTG CCC CTT
 S   L 766         775         784         793         802         811
GTC CCC ACT TCA GCC CCA GGA CCT TTC CTT GCC CTT TGG TTC CAG ATA TCA GAC 820         829         838         847
TGT TCC CTG TTC ACA GCA CCC TCA GGG TCT TAA GGT   3'
```

FIGURE 2B

```
                 11             20             29             38             47             56
5' CTG TGA TGA AAC ACT TTT CCC GTG TCG TTT GAG TGC ATC TTC TCA ACA ACC CTA 65             74             83             92            101            110
   GGA GGG TTC TTG AAG CTT TTG AGA TTA ACA ATG GCA GGA AAA TCA TCA CTT TTT
                                                 M   A   G   K   S   S   L   F 119            128            137            146            155            164
   AAA GTA ATT CTC CTT GGA GAT GGT GGA GTT GGG AAG AGT TCA CTT ATG AAC AGA
    K   V   I   L   L   G   D   G   G   V   G   K   S   S   L   M   N   R 173            182            191            200            209            218
   TAT GTA ACT AAT AAG TTT GAT ACC CAG CTC TTC CAT ACA ATA GGT GTG GAA TTT
    Y   V   T   N   K   F   D   T   Q   L   F   H   T   I   G   V   E   F 227            236            245            254            263            272
   TTA AAT AAA GAT TTG GAA GTG GAT GGA CAT TTT GTT ACC ATG CAG ATT TGG GAC
    L   N   K   D   L   E   V   D   G   H   F   V   T   M   Q   I   W   D 281            290            299            308            317            326
   ACG GCA GGT CAG GAG CGA TTC CGA AGC CTG AGG ACA CCA TTT TAC AGA GGT TCT
    T   A   G   Q   E   R   F   R   S   L   R   T   P   F   Y   R   G   S 335            344            353            362            371            380
   GAC TGC TGC CTG CTT ACT TTT AGT GTC GAT GAT TCA CAA AGC TTC CAG AAC TTA
    D   C   C   L   L   T   F   S   V   D   D   S   Q   S   F   Q   N   L 389            398            407            416            425            434
   AGT AAC TGG AAG AAA GAA TTC ATA TAT TAT GCA GAT GTG AAA GAG CCT GAG AGC
    S   N   W   K   K   E   F   I   Y   Y   A   D   V   K   E   P   E   S 443            452            461            470            479            488
   TTT CCT TTT GTG ATT CTG GGT AAC AAG ATT GAC ATA AGC GAA CGG CAG GTG TCT
    F   P   F   V   I   L   G   N   K   I   D   I   S   E   R   Q   V   S 497            506            515            524            533            542
   ACA GAA GAA GCC CAA GCT TGG TGC AGG GAC AAC GGC GAC TAT CCT TAT TTT GAA
    T   E   E   A   Q   A   W   C   R   D   N   G   D   Y   P   Y   F   E 551            560            569            578            587            596
   ACA AGT GCA AAA GAT GCC ACA AAT GTG GCA GCA GCC TTT GAG GAA GCG GTT CGA
    T   S   A   K   D   A   T   N   V   A   A   A   F   E   E   A   V   R 605            614            623            632            641            650
   AGA GTT CTT GCT ACC GAG GAT AGG TCA GAT CAT TTG ATT CAG ACA GAC ACA GTC
    R   V   L   A   T   E   D   R   S   D   H   L   I   Q   T   D   T   V
```

FIGURE 3A

```
          659            668            677            686            695            704
AAT CTT CAC CGA AAG CCC AAG CCT AGC TCA TCT TGC TGT TGA TTG TTA GAT TGT
 N   L   H   R   K   P   K   P   S   S   S   C   C 713            722            731            740            749            758
TGA TGC ATT CTA ACC AAC TCA CAC ATA TAC ACA AAA TCA ACA TGG GGA TGG AGA 767            776            785            794            803            812
AGA GAA TTA GCG TTT GCA GCA GTG TAT CAT CTA CTA ATA AAA TTA AAC TAA TGT 821            830            839            848            857            866
TGC TGC TTC ATT AGT TGG TGG GAG AAG GGA CAC ATC CAC TCT TGG AGG AAT ATA 875            884            893            902            911            920
TTT ACT CAA TAA TGG CAC CTT ACA TTT ATA AAT TGT AAC AGT TGT CTA ATA ACG 929            938            947            956            965            974
TTT CTT TAA TTT AAA TAT GTA AGT TGC AGA GCT AAT AAA TGA AAT GAC CAA GAC 983            992           1001           1010           1019           1028
TTT AAT TAT AAT AAA AAT AAG AAA CTT GAC TAT TCT AGA AGT TAT ACT TGG ATT 1037           1046           1055           1064           1073           1082
TTT TCC TGG GAA AAT GGA GAA CTA CTT TTT ATA TGT GTA TGT TTT TAT GCA ATT 1091           1100           1109           1118           1127           1136
AGC ATT GTA TTC TTG GTT CAG GGA AAT ACT TTC CTA AAG CAA TAA TGT TAG ATA 1145           1154           1163           1172
TTA AAG ATT AAA ATC TAA TGT AAA AAA AAA AAA AAA AAA   3'
```

RAB PROTEINS

FIELD OF THE INVENTION

This invention relates to nucleic acid and amino acid sequences of Rab proteins and to the use of these sequences in the diagnosis, prevention, and treatment of immune system disorders, cancer, and diseases involving vesicle, membrane, or protein movement.

BACKGROUND OF THE INVENTION

Transport of material between the different subcellular compartments of eukaryote cells often requires carrier vesicles, which bud from a donor organelle and fuse with the recipient one. Rab proteins are low molecular weight guanidine triphosphatases (GTPases) of the Ras superfamily which are localized to the membrane surfaces of organelles. They appear to be involved in the regulation of intracellular vesicular transport in both exocytic and endocytic pathways. They may also be involved in the complex and critical processes of organelle fragmentation and restructuring that occur each cell cycle. Rab proteins cycle between active GTP-bound and inactive GDP-bound conformations.

Newly formed Rab proteins associate with Rab escort proteins (REPs) in the cell cytosol. Rab proteins are then stably isoprenylated by the covalent addition of two 20-carbon geranylgeranyl groups to carboxy-terminal cysteine residues (Khosravi-Far R. et al. (1991) Proc. Natl. Acad. Sci. 88: 6264–6268). Prenylation occurs by Rab geranylgeranyl transferase (GGTase) and is essential for Rab protein function and membrane localization. A deficiency in prenylation of one particular Rab leads to choroideremia, a form of retinal degeneration that may cause blindness (Seabra M. C. et al. (1996) J. Biol. Chem. 270: 24420–24427; Seabra et al. (1993) Science 259: 377–381). Each of the more than 30 Rab proteins identified appears to have characteristic intracellular distribution and may function in distinct transport events. REPs help transfer newly prenylated Rab proteins to the appropriate organelle membrane.

The amino acid sequence of Rab proteins reveal conserved GTP-binding domains that are characteristic among Ras superfamily members (Zahraoui A. et al. (1989) J. Biol. Chem. 264: 12394–123401 Chen D. et al. (1996) Gene 174: 129–134). GTP binding or conversion from GDP to GTP form occurs en route to the organelle membrane. Experimental evidence shows that GTP-bound Rab proteins are directed into nascent transport vesicles where they interact with SNARE factors, a complex of proteins that direct vesicle targeting and fusion. Following vesicle transport, GTPase activating proteins (GAPs) in the target membrane convert Rab proteins to the GDP-bound form. A cytosolic protein, guanine-nucleotide dissociation inhibitor (GDI) helps return GDP-bound Rab proteins to their membrane of origin.

Rab proteins appear to play a role in mediating the function of a viral gene, Rev, which is essential for replication of HIV-1, the virus responsible for AIDS (Fridell R. A. et al. (1996) Proc. Natl. Acad. Sci. 93: 4421–4424). Rab proteins, when overexpressed, can significantly enhance Rev function. Furthermore, mutational analysis suggests that Rev protein has a nuclear signal domain that is necessary for localization into the cell nucleus and is likely to be a Rab protein binding site (Fridell et al., supra).

Both the inhibition of vesicle transport and organelle fragmentation during mitosis are due to an inhibition of vesicle fusion, which occurs while vesicle budding continues. Protein phosphorylation by Cdc2 protein kinase is a key regulatory event in mitosis. Toumikoski T. et al. have shown that addition of Cdc2 protein kinase to interphase cell extracts inhibits vesicle fusion (1989, Nature 342: 942–945). Furthermore, low GTP-gamma-S concentrations, which are likely to block Rab protein GTPase activity, inhibit the fusion reaction, suggesting that Rab proteins could be mediating this critical cell cycle event. Loss of cell cycle control is a key characteristic of all human cancers.

The discovery of additional Rab genes and the proteins encoded provides potential agents which are more effective than currently available therapeutic agents in the diagnosis and treatment of immune system disorders, cancer, and diseases involving vesicle targeting, membrane transfer or fusion, or protein processing, targeting, or secretion. Thus, the new Rab proteins would satisfy a need in the art by providing new means for the diagnosis, prevention, or treatment of immune system disorders, cancer, and diseases involving vesicle targeting, membrane transfer or fusion, or protein processing, targeting, or secretion.

SUMMARY OF THE INVENTION

The present invention features three Rab proteins, designated individually as HRABS-1, HRABS-2 and HRABS-3 and collectively as HRABS, and characterized as having similarity to the Rab proteins.

Accordingly, the invention features substantially purified HRABS proteins HRABS-1, HRABS-2, and HRABS-3 having the amino acid sequences shown in SEQ ID NO:1, SEQ ID NO:3, and SEQ ID NO:5, respectively.

One aspect of the invention features isolated and substantially purified polynucleotides that encode HRABS proteins- -HRABS-1, HRABS-2, and HRABS-3. In a particular aspect, the polynucleotides are the nucleotide sequences of SEQ ID NO:2, SEQ ID NO:4, and SEQ ID NO:6, respectively.

The invention also features a polynucleotide sequence comprising the complement of SEQ ID NO:2, SEQ ID NO:4, SEQ ID NO:6, or variants thereof. In addition, the invention features polynucleotide sequences which hybridize under stringent conditions to SEQ ID NO:2, SEQ ID NO:4, or SEQ ID NO:6.

The invention additionally features nucleic acid sequences encoding polypeptides, oligonucleotides, peptide nucleic acids (PNA), fragments, portions or antisense molecules thereof, and expression vectors and host cells comprising polynucleotides that encode HRABS. The present invention also features antibodies which bind specifically to HRABS, and pharmaceutical compositions comprising substantially purified HRABS. The invention also features the use of agonists and antagonists of HRABS.

BRIEF DESCRIPTION OF THE FIGURES

FIGS. 1A and 1B show the amino acid sequence (SEQ ID NO:1) and nucleic acid sequence (SEQ ID NO:2) of HRABS-1. The alignment was produced using MACDNASIS PRO software (Hitachi Software Engineering Co., Ltd., San Bruno, Calif.).

FIGS. 2A and 2B show the amino acid sequence (SEQ ID NO:3) and nucleic acid sequence (SEQ ID NO:4) of HRABS-2.

FIGS. 3A and 3B show the amino acid sequence (SEQ ID NO:5) and nucleic acid sequence (SEQ ID NO:6) of HRABS-3.

FIG. 4 shows the amino acid sequence alignments among HRABS-1 (SEQ ID NO:1), rat Rab28 (GI 1154901; SEQ ID NO:7), FIRABS-2 (SEQ ID NO:3), rabbit Rab25 (GI 436001; SEQ ID NO:8), HRABS-3 (SEQ ID NO:5), and canine Rab9 (GI 486830; SEQ ID NO:9). The alignment was produced using the multisequence alignment program of DNASTAR software (DNASTAR Inc, Madison Wis.).

DESCRIPTION OF THE INVENTION

Figure 5:
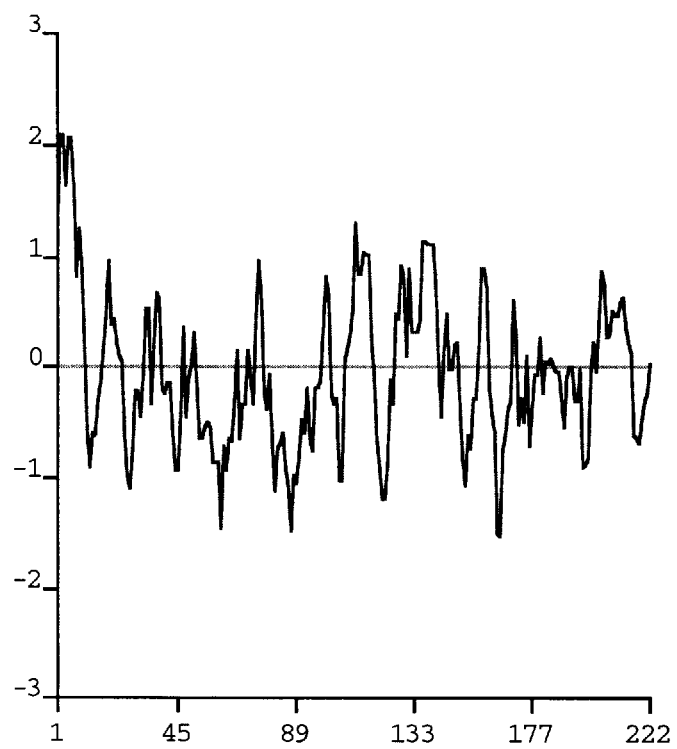
FIG. 5 shows the hydrophobicity plot (MACDNASIS PRO software) for HRABS-1, SEQ ID NO: 1; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence", as used herein, refers to an oligonucleotide, nucleotide, or polynucleotide, and fragments or portions thereof, and to DNA or RNA of genomic or synthetic origin which may be single- or double-stranded and represent the sense or antisense strand. Similarly, "amino acid sequence", as used herein, refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. "Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

HRABS, as used herein, refers to the amino acid sequences of substantially purified HRABS obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (Perkin Elmer, Norwalk, Conn.) in the 5' and/or the 3' direction and resequenced, or which has been assembled from the overlapping sequences of more than one Incyte clone using the GELVIEW Fragment Assembly system (GCG, Madison, Wis.), or which has been both extended and assembled.

A "variant" of HRABS, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HRABS, or any oligopeptide thereof, to induce a specific immune response in appropriate animals or cells and to bind with specific antibodies.

The term "agonist", as used herein, refers to a molecule which, when bound to HRABS, causes a change in HRABS which modulates the activity of HRABS. Agonists may include proteins, nucleic acids, carbohydrates, or any other molecules which bind to HRABS.

The terms "antagonist" or "inhibitor", as used herein, refer to a molecule which, when bound to HRABS, blocks or modulates the biological or immunological activity of HRABS. Antagonists and inhibitors may include proteins, nucleic acids, carbohydrates, or any other molecules which bind to HRABS.

The term "modulate", as used herein, refers to a change or an alteration in the biological activity of HRABS. Modulation may be an increase or a decrease in protein activity, a change in binding characteristics, or any other change in the biological, functional or immunological properties of HRABS.

The term "mimetic", as used herein, refers to a molecule, the structure of which is developed from knowledge of the structure of HRABS or portions thereof and, as such, is able to effect some or all of the actions of Rab-like molecules.

The term "derivative", as used herein, refers to the chemical modification of a nucleic acid encoding HRABS or the encoded HRABS. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human HRABS-1 and fragments thereof. "Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome.

They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HRABS or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), CDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding HRABS in a sample and thereby correlates with expression of the transcript from the polynucleotide encoding the protein. "Alterations" in the polynucleotide of SEQ ID NO:2, SEQ ID NO:4, or SEQ ID NO:6, as used herein, comprise any alteration in the sequence of polynucleotides encoding HRABS including deletions, insertions, and point mutations that may be detected using hybridization assays. Included within this definition is the detection of alterations to the genomic DNA sequence which encodes HRABS (e.g., by alterations in the pattern of restriction fragment length polymorphisms capable of hybridizing to SEQ ID NO:2, SEQ ID NO:4, or SEQ ID NO:6), the inability of a selected fragment of SEQ ID NO:2, SEQ ID NO:4, or SEQ ID NO:6 to hybridize to a sample of genomic DNA (e.g., using allele-specific oligonucleotide probes), and improper or unexpected hybridization, such as hybridization to a locus other than the normal chromosomal locus for the polynucleotide sequence encoding HRABS (e.g., using fluorescent in situ hybridization (FISH) to metaphase chromosome spreads).

As used herein, the term "antibody" refers to intact molecules as well as fragments thereof, such as Fa, F(ab')$_2$, and Fv, which are capable of binding the epitopic determinant. Antibodies that bind HRABS polypeptides can be prepared using intact polypeptides or fragments containing small peptides of interest as the immunizing antigen. The polypeptide or peptide used to immunize an animal can be derived from the translation of mRNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of Rab proteins (HRABS-1, HRABS-2, and HRABS-3, collectively referred to as HRABS), the polynucleotides encoding HRABS, and the use of these compositions for the diagnosis, prevention, or treatment of immune system disorders, cancer, and diseases involving vesicle targeting, membrane transfer or fusion, or protein processing, targeting, or secretion.

Nucleic acid sequence encoding the human HRABS-1 of the present invention was first identified in Incyte Clone 1780 from a U937 monocyte-like cell line cDNA library (U937NOT01) through a computer-generated search for amino acid sequence alignments. A consensus sequence, SEQ ID NO:2, was derived from the following overlapping and/or extended nucleic acid sequences (cDNA library from which derived): Incyte Clones 1780 (U937NOT01), 161560 (ADENINB01), 1457948 (COLNFET02), and 1673861 (BLADNOT05).

Nucleic acid sequence encoding the human HRABS-2 of the present invention was first identified in Incyte Clone 193787 from a kidney tissue cDNA library (KIDNNOT02) through a computer-generated search for amino acid sequence alignments. A consensus sequence, SEQ ID NO:4, was derived from the following overlapping and/or extended nucleic acid sequences (cDNA library from which derived): Incyte Clones 193787 (KIDNNOT02), 887715 (PANCNOT05), 905400 (COLNNOT08), 1309922 (COLNFET02), and 1823317 (GBLATUT01).

Nucleic acid sequence encoding the human HRABS-3 of the present invention was first identified in Incyte Clone 641412, from a breast tissue cDNA library (BRSTNOT03) through a computer-generated search for amino acid sequence alignments. A consensus sequence, SEQ ID NO:6, was derived from the following overlapping and/or extended nucleic acid sequences (cDNA library from which derived): Incyte Clones 641412 and 898935 (BRSTTUT03), 1336084 (COLNNOT13), and 2207275 (SINTFET03).

Figure 4:
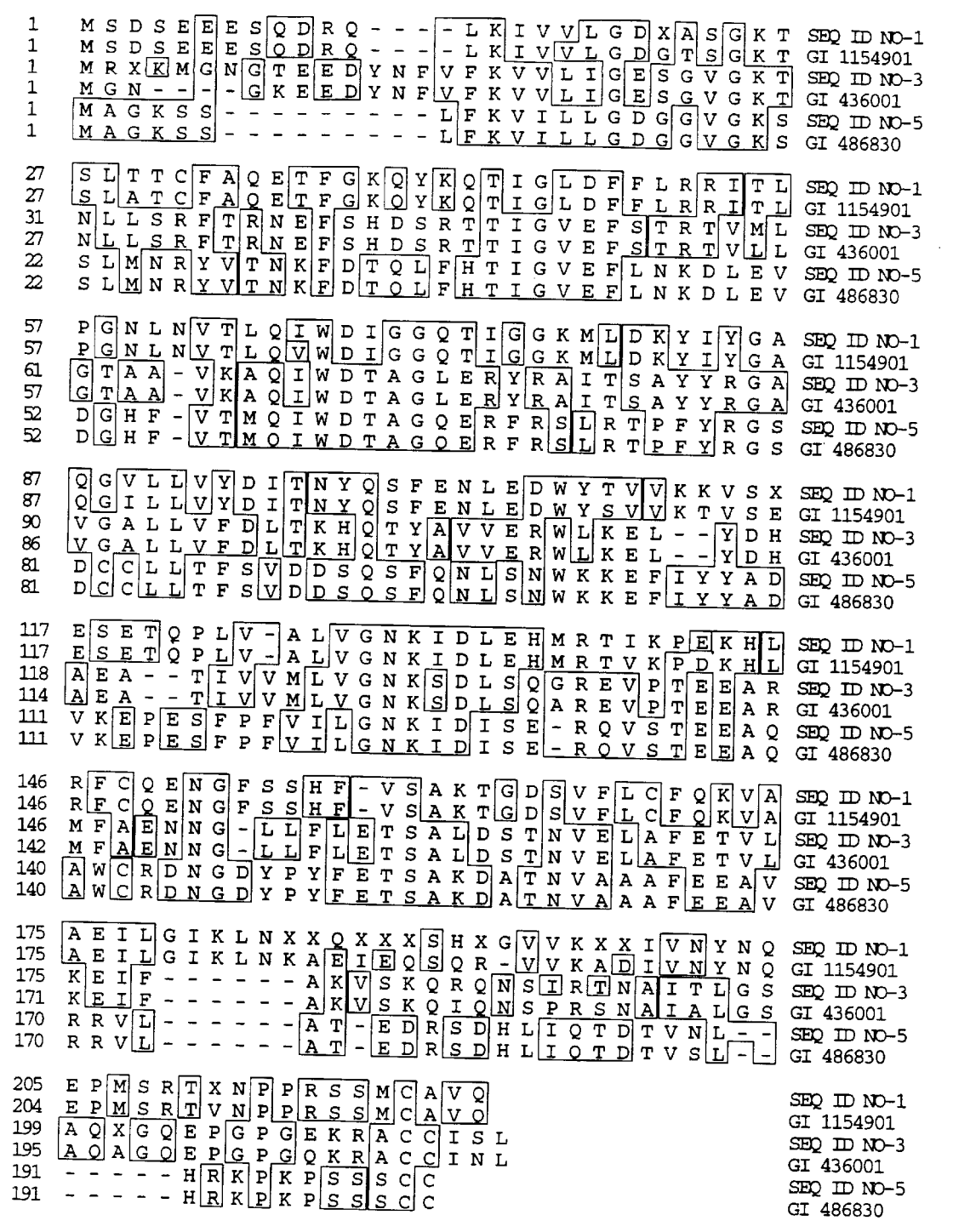
Figure 8:
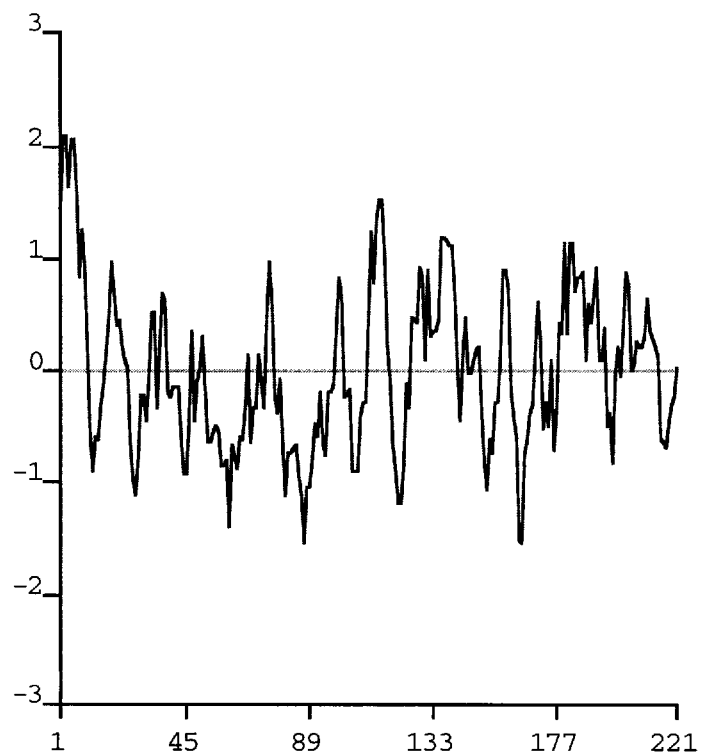
FIG. 8 shows the hydrophobicity plot for rat Rab28, SEQ ID NO:7.

In one embodiment, the invention encompasses the novel human Rab protein of HRABS-1, a polypeptide comprising the amino acid sequence of SEQ ID NO:1, as shown in FIGS. 1A and 1B. HRABS-1 is 222 amino acids in length and contains a potential N-glycosylation site at amino acid residue 61. As shown in FIG. 4, HRABS-1 has chemical and structural homology with rat Rab28 (GI 1154901; SEQ ID NO:7), rabbit Rab25 (GI 436001; SEQ ID NO:8), and canine Rab9 (GI 486830; SEQ ID NO:9). In particular, HRABS-1 shares 94% identity with rat Rab28. The homology includes conserved GTP/GDP binding domains at amino acid residues 24–26, 76–81, 128–132, and 159–160 (FIG. 4). As illustrated by FIGS. 5 and 8, HRABS-1 and rat Rab28 have similar hydrophobicity plots. Expression of HRABS-1 mRNA occurs most often in cancer associated, fetal, or immortalized cell lines, in inflamed tissues, such as adenoid or ulcerative colitis, and in cells of the immune system, such as granulocytes.

Figure 6:
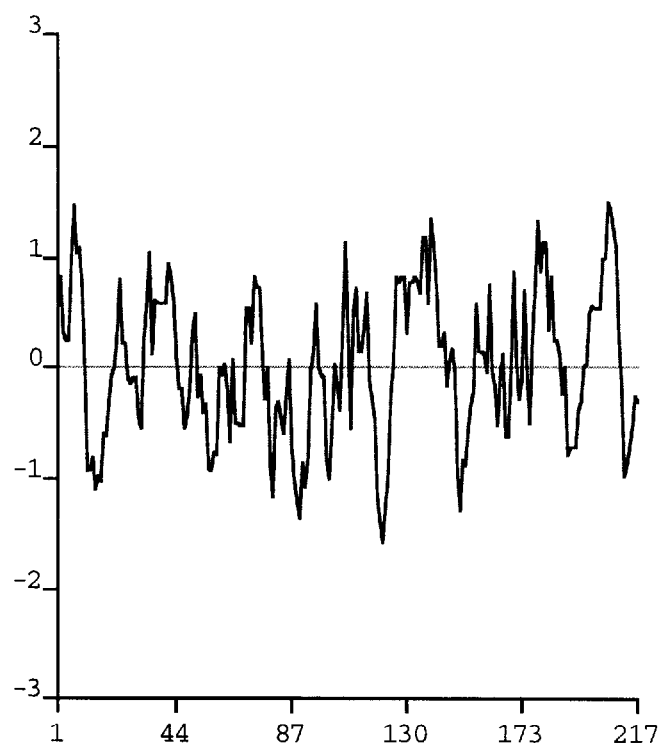
FIG. 6 shows the hydrophobicity plot for HRABS-2, SEQ ID NO:3.

In another embodiment, the invention encompasses the novel human Rab protein HRABS-2, a polypeptide comprising the amino acid sequence of SEQ ID NO:3, as shown in FIGS. 2A and 2B. HRABS-2 is 217 amino acids in length and contains potential N-glycosylation sites at amino acid residues 7 and 129. As shown in FIG. 4, HRABS-2 has chemical and structural homology with rat Rab28 (GI 1154901; SEQ ID NO:7), rabbit Rab25 (GI 436001; SEQ ID NO:8), and canine Rab9 (GI 486830; SEQ ID NO:9). In particular, HRABS-2 shares 96% identity with rabbit Rab25. The homology includes conserved GTP/GDP binding domains at amino acid residues 27–30, 70–74, 128–132, and 157–160 (FIG. 4). At residues 213 and 214, HRABS-2 has conserved carboxy-terminal cysteine residues that are suitable substrates for prenylation. As illustrated by FIGS. 6 and 8, HRABS-2 and rat Rab28 have similar hydrophobicity plots. Expression of HRABS-2 mRNA occurs most often in cancer, fetal, or dividing cells and in gastrointestinal tissues, including diseased tissue from colitis and Crohn's disease patients.

Figure 7:
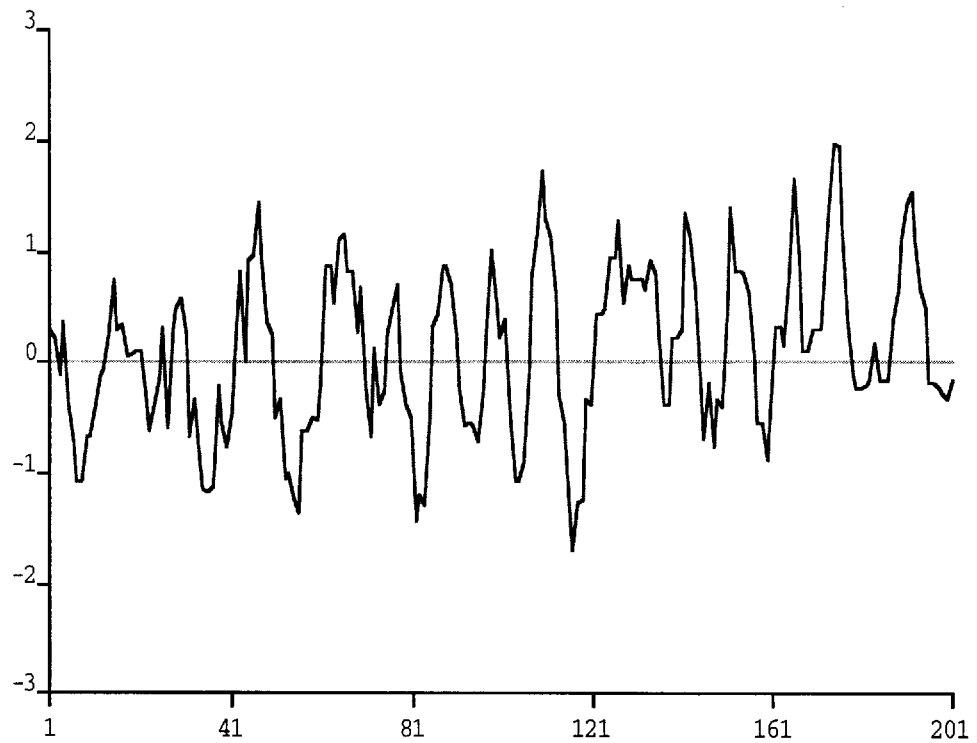
FIG. 7 shows the hydrophobicity plot for HRABS-3, SEQ ID NO:5.

In an additional embodiment, the invention encompasses the novel human Rab protein HRABS-3, a polypeptide comprising the amino acid sequence of SEQ ID NO:5, as shown in FIGS. 3A and 3B. HRABS-3 is 201 amino acids in length. As shown in FIG. 4, HRABS-3 has chemical and structural homology with rat Rab28 (GI 1154901; SEQ ID NO:7), rabbit Rab25 (GI 436001; SEQ ID NO:8), and canine Rab9 (GI 486830; SEQ ID NO:9). In particular, HRABS-3 shares 99% identity with canine Rab9. The homology includes conserved GTP/GDP binding domains at amino acid residues 18–20, 61–66, 124–128, and 152–155 (FIG. 4). At residues 200 and 201, HRABS-3 has conserved carboxy-terminal cysteine residues that are suitable substrates for prenylation. As illustrated by FIGS. 7 and 8, HRABS-3 and rat Rab28 have similar hydrophobicity plots. Expression of HRABS-3 mRNA occurs in tissues from a variety of sources, including tumors of the brain, breast, penis, and stomach.

The invention also encompasses HRABS variants. A preferred HRABS variant is one having at least 80%, and more preferably 90%, amino acid sequence similarity to the HRABS amino acid sequence (SEQ ID NO: 1, SEQ ID NO:3, or SEQ ID NO:5). A most preferred HRABS variant is one having at least 95% amino acid sequence similarity to SEQ ID NO:1, SEQ ID NO:3, or SEQ ID NO:5.

The invention also encompasses polynucleotides which encode HRABS. Accordingly, any nucleic acid sequence which encodes the amino acid sequence of HRABS can be used to generate recombinant molecules which express HRABS. In a particular embodiment, the invention encompasses the polynucleotide comprising the nucleic acid of SEQ ID NO:2, SEQ ID NO:4, or SEQ ID NO:6 as shown in FIGS. 1A, 1B, 2A, 2B, 3A, and 3B.

It will be appreciated by those skilled in the art that as a result of the degeneracy of the genetic code, a multitude of nucleotide sequences encoding HRABS, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HRABS, and all such variations are to be considered as being specifically disclosed.

Although nucleotide sequences which encode HRABS and its variants are preferably capable of hybridizing to the nucleotide sequence of the naturally occurring HRABS under appropriately selected conditions of stringency, it may be advantageous to produce nucleotide sequences encoding HRABS or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HRABS and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode HRABS and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding HRABS or any portion thereof.

Also encompassed by the invention are polynucleotide sequences that are capable of hybridizing to the claimed nucleotide sequences, and in particular, those shown in SEQ ID NO:2, SEQ ID NO:4, or SEQ ID NO:6, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–11), and may be used at a defined stringency.

Altered nucleic acid sequences encoding HRABS which are encompassed by the invention include deletions, insertions, or substitutions of different nucleotides resulting in a polynucleotide that encodes the same or a functionally equivalent HRABS. The encoded protein may also contain deletions, insertions, or substitutions of amino acid residues which produce a silent change and result in a functionally equivalent HRABS. Deliberate amino acid substitutions may be made on the basis of similarity in polarity, charge, solubility, hydrophobicity, hydrophilicity, and/or the amphipathic nature of the residues as long as the biological activity of HRABS is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine;

asparagine and glutamine; serine and threonine; phenylalanine and tyrosine.

Also included within the scope of the present invention are alleles of the gene encoding HRABS. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding HRABS may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO® 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HRABS, or fusion proteins or functional equivalents thereof, may be used in recombinant DNA molecules to direct expression of HRABS in appropriate host cells. Due to the inherent degeneracy of the genetic code, other DNA sequences which encode substantially the same or a functionally equivalent amino acid sequence may be produced and these sequences may be used to clone and express HRABS.

As will be understood by those of skill in the art, it may be advantageous to produce HRABS-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter sequences encoding HRABS for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, to alter glycosylation patterns, to change codon preference, to produce splice variants, or to introduce mutations, and so forth.

In another embodiment of the invention, natural, modified, or recombinant polynucleotides encoding HRABS may be ligated to a heterologous sequence to encode a fusion protein. For example, to screen peptide libraries for inhibitors of HRABS activity, it may be useful to encode a chimeric HRABS protein that can be recognized by a commercially available antibody. A fusion protein may also be engineered to contain a cleavage site located between a sequence encoding HRABS and the heterologous protein sequence, so that HRABS may be cleaved and purified away from the heterologous moiety.

In another embodiment, sequences encoding HRABS may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HRABS, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of HRABS, or any part thereof, may be altered during direct synthesis and/or combined using chemical methods with sequences from other proteins, or any part thereof, to produce a variant polypeptide.

In order to express a biologically active HRABS, the nucleotide sequences encoding HIRABS or functional equivalents, may be inserted into appropriate expression vectors, i.e., a vector which contains the necessary elements for the transcription and translation of the inserted coding sequence.

Methods which are well known to those skilled in the art may be used to construct expression vectors containing sequences encoding HRABS and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding HRABS. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL), and the like, may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HRABS, vectors based on SV40 or EBV may be used with an appropriate selectable marker.

In bacterial systems, a number of expression vectors may be selected depending upon the use intended for HRABS. For example, when large quantities of HRABS are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding HRABS may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding HRABS may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express HRABS. For example, in one such system, *Autographa californica* nuclear polyhedrosis virus (AcNPV) is used as a vector to express foreign genes in *Spodoptera frugiperda* cells or in Trichoplusia larvae. The sequences encoding HRABS may be cloned into a non-essential region of the virus, such as the polyhedrin gene, and placed under control of the polyhedrin promoter. Successful insertion of HRABS will render the polyhedrin gene inactive and produce recombinant virus lacking coat protein. The recombinant viruses may then be used to infect, for example, *S. frugiperda* cells or Trichoplusia larvae in which HRABS may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HRABS may be ligated into an adenovirus transcription/translation complex consisting of the late promoter and tripartite leader sequence. Insertion in a non-essential E1 or E3 region of the viral genome may be used to obtain a viable virus which is capable of expressing HRABS in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding HRABS. Such signals include the ATG initiation codon and adjacent sequences. In cases where sequences encoding HRABS, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HRABS may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, βglucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HRABS is inserted within a marker gene sequence, recombinant cells containing sequences encoding HRABS can be identified by the absence of marker gene function. Alternatively, a marker gene can be placed in tandem with a sequence encoding HRABS under the control of a single promoter. Expression of the marker gene in response to induction or selection usually indicates expression of the tandem gene as well.

Alternatively, host cells which contain sequences encoding and expressing HRABS may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of the nucleic acid or protein.

The presence of polynucleotide sequences encoding HRABS can be detected by DNA-DNA or DNA-RNA hybridization or amplification using probes or portions or fragments of polynucleotides encoding HRABS. Nucleic acid amplification based assays involve the use of oligonucleotides or oligomers based on the sequences encoding HRABS to detect transformants containing DNA or RNA encoding HRABS. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HRABS, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HRABS is preferred, but a competitive binding assay may be employed. These and other assays are described, among other places, in Hampton, R. et al. (1990; *Serological Methods, a Laboratory Manual,* APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HRABS include oligolabeling, nick translation, end-labeling or PCR amplification using a labeled nucleotide. Alternatively, sequences encoding HRABS, or any portion thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.); Promega (Madison, Wis.); and U.S. Biochemical Corp. (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding HRABS may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HRABS may be designed to contain signal sequences which direct secretion of HRABS through a prokaryotic or eukaryotic cell membrane. Other recombinant constructions may be used to join sequences encoding HRABS to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HPABS may be used to facilitate purification. One such expression vector provides for expression of a fusion protein containing HRABS and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying HRABS from the fusion protein. A discussion of vectors which contain fusion proteins is provided in Kroll, D. J. et al. (1993; DNA Cell Biol. 12:441–453).

In addition to recombinant production, fragments of HRABS may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431 A Peptide Synthesizer (Perkin Elmer). Various fragments of HRABS may be chemically synthesized separately and combined using chemical methods to produce the full length molecule.

THERAPEUTICS

Based on the chemical and structural homology among HRABS, rat Rab28, rabbit Rab25, and canine Rab9, HRABS appears to play a role in immune system disorders, cancer, and diseases involving vesicle targeting, membrane transfer or fusion, or protein processing, targeting, or secretion.

HRABS have a role in the movement of vesicles, membranes, and proteins. Therefore, in one embodiment, HRABS or derivatives thereof may be administered to a subject to treat disorders involving vesicle targeting, membrane transfer or fusion, or protein processing, targeting, or secretion. Such disorders include, but are not limited to, conditions which are characterized by abnormal levels of neurotransmitter production and release, lysosomal storage diseases, choroideremia, and endocrine hypofunction and hyperfunction.

In another embodiment, antagonists of HRABS may be administered to a subject to treat immune system disorders including, but not limited to, autoimmune hemolytic anemia, juvenile diabetes mellitus, lupus erythematosus, multiple sclerosis, myasthenia gravis, Crohn's disease, rheumatoid arthritis, and AIDS.

In another embodiment, antagonists of HRABS may be administered to a subject to treat cancers including, but not limited to, leukemia, lymphoma, and carcinomas of the lung, penis, breast, pancreas, colon, stomach, small intestine, brain, and prostate.

In another aspect, antibodies which are specific for HRABS may be used directly as an antagonist, or indirectly as a targeting or delivery mechanism for administering a pharmaceutical agent to cells or tissue which express HRABS.

In another embodiment, vectors expressing antisense to the nucleic acid sequence encoding HRABS or a fragment or derivative thereof may be administered to a subject to treat immune system diseases or cancers previously described.

In another embodiment, vectors expressing HRABS may be administered to a subject to treat disorders resulting from a deficiency of HRABS expression which may include, but are not limited to, diseases involving vesicle targeting, membrane transfer or fusion, or protein processing, targeting, or secretion.

Antagonists or inhibitors of HRABS may be produced using methods which are generally known in the art. In particular, purified HRABS may be used to produce antibodies or to screen libraries of pharmaceutical agents to identify those which specifically bind HRABS.

Antibodies which are specific for HRABS may be used directly as an antagonist, or indirectly as a targeting or delivery mechanism for bringing a pharmaceutical agent to cells or tissue which express HRABS. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HRABS or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HRABS have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HRABS amino acids may be fused with those of another protein such as keyhole limpet hemocyanin and antibody produced against the chimeric molecule.

Monoclonal antibodies to HRABS may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J Immunol. Methods 81:31–42; Cote, R. J. et al. (1983) Proc. Natl. Acad. Sci. 80:2026–2030; Cole, S. P. et al. (1985) Mol Cell Biol. 62:109–120.

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–55; Neuberger, M. S. et al. (1984) Nature 312:604–8; Takeda, S. et al. (1985) Nature 314:452–4). Alternatively, techniques described for the production of single chain antibodies may be adapted, using methods known in the art, to produce HRABS-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–37; Winter, G. et al. (1991) Nature 349:293–9).

Antibody fragments which contain specific binding sites for HRABS may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments.

Alternatively, Fab expression libraries may be constructed to allow rapid and easy identification of monoclonal Fab fragments with the desired specificity (Huse, W. D. et al. (1989) Science 254:1275–81).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HRABS and its specific antibody. A two-site, monoclonal-based immunoassay utilizing monoclonal antibodies reactive to two non-interfering HRABS epitopes is preferred, but a competitive binding assay may also be employed (Maddox, supra).

In another embodiment of the invention, the polynucleotides encoding HRABS, or any fragment thereof, or antisense molecules, may be used for therapeutic purposes. In one aspect, antisense to the polynucleotide encoding HRABS may be used in situations in which it would be desirable to block the transcription of mRNA. In particular, cells may be transformed with sequences complementary to polynucleotides encoding HRABS. Thus, antisense sequences may be used to modulate HRABS activity, or to achieve regulation of gene function. Such technology is now well known in the art, and sense or antisense oligomers or larger fragments, can be designed from various locations along the coding or control regions of sequences encoding HRABS.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding HRABS. These techniques are described both in Sambrook et al. (supra) and in Ausubel et al. (supra).

Genes encoding native HRABS can be turned off by transforming a cell or tissue with expression vectors which express high levels of the polynucleotide, or fragment thereof, which encodes HRABS. Such constructs may be used to introduce untranslatable sense or antisense sequences into a cell. Even in the absence of integration into the genomic DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HRABS, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HRABS.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HRABS. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HRABS, antibodies to HRABS, mimetics, agonists, antagonists, or inhibitors of HRABS. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, P.a.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HRABS, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HRABS or fragments thereof, antibodies of HRABS, agonists, antagonists or inhibitors of HRABS, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HRABS may be used for the diagnosis of conditions or diseases characterized by expression of HRABS, or in assays to monitor patients being treated with HRABS, agonists, antagonists or inhibitors. The antibodies useful for diagnostic purposes may be prepared in the same manner as those described above for therapeutics. Diagnostic assays for HRABS include methods which utilize the antibody and a label to detect HRABS in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HRABS are known in the art and provide a basis for diagnosing altered or abnormal levels of HRABS expression. Normal or standard values for HRABS expression are established by combining body fluids or cell extracts taken from normal mammalian subjects, preferably human, with antibody to HRABS under conditions suitable for complex formation. The amount of standard complex formation may be quantified by various methods, but preferably by photometric means. Quantities of HRABS expressed in subject sample, control and disease, from biopsied tissues are compared with the standard values. Deviation between standard and subject values establishes the parameters for diagnosing disease.

In another embodiment of the invention, the polynucleotides encoding HRABS may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HRABS may be correlated with disease. The diagnostic assay may be used to distinguish between absence, presence, and excess expression of HRABS, and to monitor regulation of HRABS levels during therapeutic intervention.

In one aspect, hybridization with PCR probes which are capable of detecting polynucleotide sequences, including genomic sequences, encoding HRABS or closely related molecules, may be used to identify nucleic acid sequences which encode HRABS. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HRABS, alleles, or related sequences.

Probes may also be used for the detection of related sequences, and should preferably contain at least 50% of the nucleotides from any of the sequences encoding HRABS. The hybridization probes of the subject invention may be DNA or RNA and derived from the nucleotide sequences of SEQ ID NO:2, SEQ ID NO:4, or SEQ ID NO:6 or from genomic sequence including promoter, enhancer elements, and introns of the naturally occurring HRABS.

Means for producing specific hybridization probes for DNAs encoding HRABS include the cloning of nucleic acid sequences encoding HRABS or HRABS derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HRABS may be used for the diagnosis of conditions or diseases which are associated with expression of HRABS. Examples of such conditions or diseases include cancers of the lung, penis, breast, pancreas, colon, stomach, small intestine, brain, and prostate, and diseases associated with immune system disorders, such as Crohn's disease, rheumatoid arthritis, and inflamed tissue, such as in ulcerative colitis. The polynucleotide sequences encoding HRABS may be used in Southern or northern analysis, dot blot, or other membrane-based technologies; in PCR technologies; or in dip stick, pIN, ELISA or chip assays utilizing fluids or tissues from patient biopsies to detect altered HRABS expression. Such qualitative or quantitative methods are well known in the art.

In a particular aspect, the nucleotide sequences encoding HRABS may be useful in assays that detect activation or induction of various cancers, particularly those mentioned above. The nucleotide sequences encoding HRABS may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HRABS in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HRABS, a normal or standard profile for expression is established. This may be accomplished by combining body fluids or cell extracts taken from normal subjects, either animal or human, with a sequence, or a fragment thereof, which encodes HRABS, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively low amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HRABS may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HRABS include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequence which encodes HRABS may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma, R. S. et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding HRABS on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HRABS, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HRABS and the agent being tested, may be measured.

Another technique for drug screening which may be used provides for high throughput screening of compounds having suitable binding affinity to the protein of interest as described in published PCT application W084/03564. In this method, as applied to HRABS large numbers of different small test compounds are synthesized on a solid substrate, such as plastic pins or some other surface. The test compounds are reacted with HRABS, or fragments thereof, and washed. Bound HRABS is then detected by methods well known in the art. Purified HRABS can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HRABS specifically compete with a test compound for binding HRABS. In this manner, the antibodies can be used to detect the presence of any peptide which shares one or more antigenic determinants with HRABS.

In additional embodiments, the nucleotide sequences which encode HRABS may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES
I DNA Library Construction
U937NOT01

The human lymphoma U-937 cDNA library is commercially available from Stratagene (catalogue #937207). Poly (A+)RNA was purified from U-937 cells and then used to synthesize double stranded complementary DNA (cDNA). Synthetic adaptor oligonucleotides were ligated onto cDNAs which were inserted into the Uni-ZAPT vector system (Stratagene). The custom-constructed library phage particles were transfected into E. coli host strain XL1-BLUE (Stratagene).
KIDNNOT02

The normal kidney used for this library was obtained from the Keystone Skin Bank, International Institute for the Advancement of Medicine (Exton, P.a.). Normal kidney tissue from a 64 year old Caucasian female (Lot HEF698) was flash frozen, ground in a mortar and pestle, and lysed immediately in buffer containing guanidinium isothiocyanate. Lysis was followed by several phenol chloroform extractions and ethanol precipitation. Poly A+ RNA was isolated using biotinylated oligo d(T) primer and streptavidin coupled to a paramagnetic particle (Promega Corp, Madison Wis.) and sent to Stratagene.

Stratagene prepared the cDNA library using oligo d(T) priming. Synthetic adapter oligonucleotides were ligated onto the cDNA molecules enabling them to be inserted into the UNI-ZAP—vector system (Stratagene). The quality of the cDNA library was screened using DNA probes, and then, the pBluescript phagemid (Stratagene) was excised. Subsequently, the custom constructed library phage particles were infected into E. coli host strain XL1-BLUE (Stratagene). Alternative unidirectional vectors might include, but are not limited to, pcDNAI (Invitrogen, San Diego, Calif.) and pSHlox-1 (Novagen, Madison Wis.).
BRSTNOT03

The BRSTNOT03 cDNA library was constructed from tissue removed from the normal breast of a 54 year old female. The frozen tissue was immediately homogenized and lysed using a Brinkmann Homogenizer Polytron PT-3000 (Brinkmann Instruments Inc, Westbury N.Y.) in guanidinium isothiocyanate solution. Lysates were then loaded on a 5.7M CsCl cushion and ultracentrifuged in a SW28 swinging bucket rotor for 18 hours at 25,000 rpm at ambient temperature. The RNA was extracted once with acid phenol at pH 4.0 and once with phenol chloroform at pH 8.0 and precipitated using 0.3M sodium acetate and 2.5 volumes of ethanol, resuspended in DEPC-treated water and DNase treated for 25 min at 37° C. The reaction was stopped with an equal volume of acid phenol, and the RNA was isolated using the Qiagen OLIGOTEX kit (QIAGEN Inc, Chatsworth Calif.) and used to construct the cDNA library.

The RNA was handled according to the recommended protocols in the SuperScript Plasmid System for cDNA Synthesis and Plasmid Cloning (Cat. #18248-013; Gibco/BRL). cDNAs were fractionated on a SEPHAROSE CL4B column (Cat. #275105, Pharmacia), and those cDNAs exceeding 400 bp were ligated into PSPORT1. The plasmid PSPORT1 was subsequently transformed into DH5α™ competent cells (Cat. #18258-012, Gibco/BRL).
II Isolation and Sequencing of cDNA Clones
U937NOT01 and KIDNNOT02

The phagemid forms of individual cDNA clones were obtained by the in vivo excision process, in which the host bacterial strain was coinfected with both the lambda library phage and an f1 helper phage. Polypeptides derived from both the library-containing phage and the helper phage nicked the lambda DNA, initiated new DNA synthesis from defined sequences on the lambda target DNA and created a smaller, single stranded circular phagemid DNA molecule that included all DNA sequences of the PBLUESCRIPT plasmid and the cDNA insert. The phagemid DNA was secreted from the cells and purified, then used to re-infect fresh host cells, where the double stranded phagemid DNA was produced. Because the phagemid carries the gene for β-lactamase, the newly-transformed bacteria are selected on medium containing ampicillin.

Phagemid DNA was purified using the MAGIC MINI-PREPS DNA Purification System (catalogue #A7100. Promega Corp., Madison, Wis.). The DNA was eluted from the purification resin already prepared for DNA sequencing and other analytical manipulations.

Phagemid DNA was also purified using the QIAWELL-8, QIAWELL PLUS, and QIAWELL ULTRA DNA Purification System (QIAGEN). The DNA was eluted from the purification resin already prepared for DNA sequencing and other analytical manipulations.

BRSTNOT03

Plasmid DNA was released from the cells and purified using the Miniprep Kit (Cat. #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat. #22711, LIFE TECHNOLOGIES, Gaithersburg Md.) with carbenicillin at 25 mg/L and glycerol at 0.4%; 2) the bacteria were cultured for 24 hours after the wells were inoculated and then lysed with 60 $\mu$l of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F. and A. R. Coulson (1975; J. Mol. Biol. 94:441f), using a Hamilton Micro Lab 2200 (Hamilton, Reno Nev.) in combination with four Peltier Thermal Cyclers (PTC200; MJ Research, Watertown Mass.) and Applied Biosystems 377 or 373 DNA Sequencing Systems (Perkin Elmer), and reading frame was determined.

III Homology Searching of cDNA Clones and Their Deduced Proteins

U937NOT01

The cDNA inserts from random isolates of the U-937 library were sequenced in part. Methods for DNA sequencing are well known in the art. Conventional enzymatic methods employ DNA polymerase Klenow fragment, SEQUENASE or Taq polymerase to extend DNA chains from an oligonucleotide primer annealed to the DNA template of interest. The chain termination reaction products are electrophoresed on urea-acrylamide gels and are detected either by autoradiography (for radionuclide-labelled precursors) or by fluorescence (for fluorescent-labelled precursors).

The cDNA clones obtained from the U-937 library originate from essentially random initiation and termination events. Therefore, the reading frame contained within the clone might be, in some cases, ambiguous. In these cases, the reading frame can be ascertained by several types of analyses. First, reading frames contained within the coding sequence can be analyzed for the presence of start (ATG, GTG, etc.) and stop codons (TGA, TAA, TAG). Typically, one frame will continue throughout the major portion of all of a cDNA sequence and the other two pending frames tend to contain numerous stop codons. In these cases reading frame determination is straightforward. In other more difficult cases, frame determination may require further analysis. Algorithms for this purpose have been developed which analyze the occurrence of individual nucleotide bases at each putative codon triplet.

KIDNNOT02 and BRSTNOT03

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul S. F. (1993) J. Mol. Evol. 36:290–300; Altschul, S. F. et al. (1990) J. Mol. Biol. 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (1993; Proc. Natl. Acad. Sci. 90:5873–7) and incorporated herein by reference, searches matches between a query sequence and a database sequence, to evaluate the statistical significance of any matches found, and to report only those matches which satisfy the user-selected threshold of significance. In this application, threshold was set at 10–25 for nucleotides and 10–14 for peptides.

Incyte nucleotide sequence were searched against the GenBank databases for pri=primate, rod=rodent, and mam=mammalian sequences, and deduced amino acid sequences from the same clones are searched against GenBank functional protein databases, mamp=mammalian, vrtp=vertebrate and eukp=eukaryote, for homology. The relevant database for a particular match were reported as a GIxxx+p (where xxx is for pri, rod, etc and if present, p=peptide). The product score=(% nucleotide or amino acid identity [between the query and reference sequences] in Blast multiplied by the % maximum possible BLAST score [based on the lengths of query and reference sequences]) divided by 100. Where an Incyte Clone was homologous to several sequences, up to five matches were provided with their relevant scores. In an analogy to the hybridization procedures used in the laboratory, a conservative electronic stringency was set at 70 ("exact" match), and the cutoff was set at approximately 40 (with 1–2% error due to uncalled bases).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HRABS occurs.

Abundance and percent abundance are also reported. Abundance directly reflects the number of times a particular transcript is represented in a cDNA library, and percent abundance is abundance divided by the total number of sequences examined in the cDNA library.

V Extension of Polynucleotides Encoding HRABS to Full Length or to Recover Regulatory Sequences Polynucleotides encoding HRABS (SEQ ID NO:2, SEQ ID NO:4, or SEQ ID NO:6) are used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK KIT (Qiagen Inc.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 μCi of [γ-$^{32}$p] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the sequence encoding HRABS, or any part thereof, is used to inhibit in vivo or in vitro expression of naturally occurring HRABS. Although use of antisense oligonucleotides, comprising about 20 base-pairs, is specifically described, essentially the same procedure is used with larger cDNA fragments. An oligonucleotide based on the sequences encoding HRABS is used to inhibit expression of naturally occurring HRABS. The complementary oligonucleotide is designed from the most unique 5' sequence as shown in and used either to inhibit transcription by preventing promoter binding to the upstream nontranslated sequence or translation of a transcript encoding HRABS by preventing the ribosome from binding. Using an appropriate portion of the signal and 5' sequence of SEQ ID NO:2, SEQ ID NO:4, or SEQ ID NO:6, an effective antisense oligonucleotide includes any 15–20 nucleotides spanning the region which translates into the signal or 5' coding sequence of the polypeptide as shown in FIGS. 1A, 1B, 2A, 2B, 3A, and 3B.

VIII Expression of HRABS

Expression of HRABS is accomplished by subcloning the cDNAs into appropriate vectors and transforming the vectors into host cells. In this case, the cloning vector, PSPORT, previously used for the generation of the cDNA library is used to express HRABS in *E. coli.* Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HRABS into the bacterial growth media which can be used directly in the following assay for activity.

IX Demonstration of HRABS Activity

HRABS GTP binding activity can be assayed by a technique described by Brauers A. et al. (1996, Eur. J. Biochem. 237: 833–840). Samples of 10 ug HRABS are incubated with tracer 35S guanosine 5'-O-[gamma-thio] triphosphate ([$^{35}$S] GTP[S]; 300,000 cpm/sample) in a buffer containing 20 mM $MgCl_2$, 1 mM dithiothreitol and 0.1% Triton X-100 in a total volume of 100 ml. Unlabeled GTP[S] is added, and the binding is allowed to proceed at 30° C. for 1 hour. The reaction is terminated by addition of 1 ml ice-cold buffer containing 20 mM Tris, pH 8.0, 100 mM NaCl and 25 mM $MgCl_2$. The samples are filtered through nitrocellulose membranes and washed four times with 1 ml buffer. Samples are placed in scintillation cocktail and radioactivity is measured by scintillation counting.

X Production of HRABS Specific Antibodies

HRABS that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HRABS Using Specific Antibodies

Naturally occurring or recombinant HRABS is substantially purified by immunoaffinity chromatography using antibodies specific for HRABS. An immunoaffinity column is constructed by covalently coupling HRABS antibody to an activated chromatographic resin, such as CnBr-activated SEPHAROSE (Pharmacia & Upjohn). After the coupling, the resin is blocked and washed according to the manufacturer's instructions.

Media containing HRABS is passed over the immunoaffinity column, and the column is washed under conditions that allow the preferential absorbance of HRABS (e.g., high ionic strength buffers in the presence of detergent). The column is eluted under conditions that disrupt antibody/HRABS binding (eg, a buffer of pH 2–3 or a high concentration of a chaotrope, such as urea or thiocyanate ion), and HRABS is collected.

XII Identification of Molecules Which Interact with HRABS

HRABS or biologically active fragments thereof are labeled with $^{125}$I Bolton-Hunter reagent (Bolton, A. E. and W. M. Hunter (1973) Biochem. J. 133: 529–39). Candidate molecules previously arrayed in the wells of a multi-well plate are incubated with the labeled HRABS, washed and any wells with labeled HRABS complex are assayed. Data obtained using different concentrations of HRABS are used to calculate values for the number, affinity, and association of HRABS with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide consisting of the amino acid sequence of SEQ ID NO:1.

2. A hybridization probe comprising the polynucleotide sequence of claim 1.

3. An isolated and purified polynucleotide sequence comprising SEQ ID NO:2.

4. An isolated and purified polynucleotide sequence which is fully complementary to the polynucleotide sequence of claim 1.

5. A hybridization probe comprising the polynucleotide sequence of claim 4.

6. An expression vector containing the polynucleotide sequence of claim 2.

7. A host cell containing the expression vector of claim 6.

8. A method for producing a polypeptide consisting of the amino acid sequence of SEQ ID NO:1, the method comprising the steps of:
   a) culturing the host cell of claim 7 under conditions suitable for the expression of the polypeptide; and
   b) recovering the polypeptide from the host cell culture.

9. A method for detection of a polynucleotide encoding a polypeptide consisting of the amino acid sequence of SEQ ID NO:1 in a biological sample containing nucleic acid material, the method comprising the steps of:
   a) hybridizing the polynucleotide of claim 4 to the nucleic acid material of the biological sample, thereby forming a hybridization complex; and
   b) detecting the hybridization complex, wherein the presence of the hybridization complex correlates with the presence of the polynucleotide in the biological sample.

10. An isolated and purified polynucleotide sequence encoding a polypeptide consisting of the amino acid sequence of SEQ ID NO:3.

11. A hybridization probe comprising the polynucleotide sequence of claim 10.

12. An isolated and purified polynucleotide sequence comprising SEQ ID NO:4.

13. An isolated and purified polynucleotide sequence which is fully complementary to the polynucleotide of claim 10.

14. A hybridization probe comprising the polynucleotide sequence of claim 13.

15. An expression vector containing the polynucleotide sequence of claim 10.

16. A host cell containing the expression vector of claim 15.

17. A method for producing a polypeptide consisting of the amino acid sequence of SEQ ID NO:3, the method comprising the steps of:
   a) culturing the host cell of claim 16 under conditions suitable for the expression of the polypeptide; and
   b) recovering the polypeptide from the host cell culture.

18. A method for detection of a polynucleotide encoding a polypeptide consisting of the amino acid sequence of SEQ ID NO:3 in a biological sample containing nucleic acid material, the method comprising the steps of:
   a) hybridizing the polynucleotide of claim 13 to the nucleic acid material of the biological sample, thereby forming a hybridization complex; and
   b) detecting the hybridization complex, wherein the presence of the hybridization complex correlates with the presence of the polynucleotide in the biological sample.

* * * * *

UNITED STATES PATENT AND TRADEMARK OFFICE
CERTIFICATE OF CORRECTION

PATENT NO. : 5,869,291

DATED : February 9, 1999

INVENTOR(S) : Hillman et al.

It is certified that error appears in the above-identified patent and that said Letters Patent is hereby corrected as shown below:

Col. 47, line 15, replace "claim 2" with --claim 1--.
Col. 48, line 23, replace "SEO" with --SEQ--.

Signed and Sealed this

Eleventh Day of April, 2000

Attest:

Q. TODD DICKINSON

Attesting Officer

Director of Patents and Trademarks

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:

(A) LENGTH: 222 amino acids
(B) TYPE: amino acid
(C) STRANDEDNESS: single
(D) TOPOLOGY: linear (vii) IMMEDIATE SOURCE:
(A) LIBRARY: Consensus
(B) CLONE: Consensus (xi) SEQUENCE DESCRIPTION: SEQ ID NO:1:

| Met | Ser | Asp | Ser | Glu | Glu | Ser | Gln | Asp | Arg | Gln | Leu | Lys | Ile | Val |
| 1 | | | | 5 | | | | | 10 | | | | | 15 |

| Val | Leu | Gly | Asp | Xaa | Ala | Ser | Gly | Lys | Thr | Ser | Leu | Thr | Thr | Cys | Phe |
| | | | 20 | | | | | 25 | | | | | 30 | | |

| Ala | Gln | Glu | Thr | Phe | Gly | Lys | Gln | Tyr | Lys | Gln | Thr | Ile | Gly | Leu | Asp |
| | | 35 | | | | | 40 | | | | | 45 | | | |

| Phe | Phe | Leu | Arg | Arg | Ile | Thr | Leu | Pro | Gly | Asn | Leu | Asn | Val | Thr | Leu |
| | 50 | | | | | 55 | | | | | 60 | | | | |

| Gln | Ile | Trp | Asp | Ile | Gly | Gly | Gln | Thr | Ile | Gly | Gly | Lys | Met | Leu | Asp |
| 65 | | | | | 70 | | | | | 75 | | | | | 80 |

| Lys | Tyr | Ile | Tyr | Gly | Ala | Gln | Gly | Val | Leu | Leu | Val | Tyr | Asp | Ile | Thr |
| | | | | 85 | | | | | 90 | | | | | 95 | |

| Asn | Tyr | Gln | Ser | Phe | Glu | Asn | Leu | Glu | Asp | Trp | Tyr | Thr | Val | Val | Lys |
| | | | 100 | | | | | 105 | | | | | 110 | | |

| Lys | Val | Ser | Xaa | Glu | Ser | Glu | Thr | Gln | Pro | Leu | Val | Ala | Leu | Val | Gly |
| | | 115 | | | | | 120 | | | | | 125 | | | |

| Asn | Lys | Ile | Asp | Leu | Glu | His | Met | Arg | Thr | Ile | Lys | Pro | Glu | Lys | His |
| | 130 | | | | | 135 | | | | | 140 | | | | |

| Leu | Arg | Phe | Cys | Gln | Glu | Asn | Gly | Phe | Ser | Ser | His | Phe | Val | Ser | Ala |
| 145 | | | | | 150 | | | | | 155 | | | | | 160 |

| Lys | Thr | Gly | Asp | Ser | Val | Phe | Leu | Cys | Phe | Gln | Lys | Val | Ala | Ala | Glu |
| | | | | 165 | | | | | 170 | | | | | 175 | |

| Ile | Leu | Gly | Ile | Lys | Leu | Asn | Xaa | Xaa | Gln | Xaa | Xaa | Xaa | Ser | His | Xaa |
| | | | 180 | | | | | 185 | | | | | 190 | | |

| Gly | Val | Val | Lys | Xaa | Xaa | Ile | Val | Asn | Tyr | Asn | Gln | Glu | Pro | Met | Ser |
| | | | 195 | | | | | 200 | | | | | 205 | | |

| Arg | Thr | Xaa | Asn | Pro | Pro | Arg | Ser | Ser | Met | Cys | Ala | Val | Gln |
| | 210 | | | | | 215 | | | | | 220 | | |

(2) INFORMATION FOR SEQ ID NO:2:

(i) SEQUENCE CHARACTERISTICS:
(A) LENGTH: 914 base pairs
(B) TYPE: nucleic acid
(C) STRANDEDNESS: single
(D) TOPOLOGY: linear (vii) IMMEDIATE SOURCE:
(A) LIBRARY: Consensus
(B) CLONE: Consensus (xi) SEQUENCE DESCRIPTION: SEQ ID NO:2:

| ATGGCGCTTG | CCGAGTGATT | CTCCTCGAAT | ACCTCCTGCC | GGCGCGGAGA | CACCGGGGCG | 60 |
| GGGGTCCTGC | CGCAACTACC | TCCCTTCCTC | CTCTCCCCCG | CCCCCGGAGC | CTTCATCCTT | 120 |
| CCCTTCCCCC | CCCACCTCGA | GGGGCGGGCC | TGGTTCCCGG | ACACCATGT | CGGACTCTGA | 180 |
| GGAGGAGAGC | CAGGACCGGC | AACTGAAAAT | CGTCGTGCTG | GGGGACGNNG | CCTCCGGGAA | 240 |
| GACCTCCTTA | ACTACGTGTT | TTGCTCAAGA | AACTTTTGGG | AAACAGTACA | AACAAACTAT | 300 |
| AGGACTGGAT | TTCTTTTTGA | GAAGGATAAC | ATTGCCAGGA | AACTTGAATG | TTACCCTTCA | 360 |

-continued

```
AATTTGGGAT  ATAGGAGGGC  AGACAATAGG  AGGCAAAATG  TTGGATAAAT  ATATCTATGG      420

AGCACAGGGA  GTCCTCTTGG  TATATGATAT  TACAAATTAT  CAAAGCTTTG  AGAATTTAGA      480

AGATTGGTAT  ACTGTGGTGA  AGAAAGTGAG  CNAGGAGTCA  GAAACTCAGC  CACTGGTTGC      540

CTTGGTAGGC  AATAAAATTG  ATTTGGAGCA  TATGCGAACA  ATAAAACCTG  AAAAACACTT      600

ACGGTTTTGC  CAGGAAAATG  GTTTTAGTAG  CCACTTTGTC  TCAGCCAAGA  CAGGAGACTC      660

TGTCTTCCTG  TGCTTTCAGA  AAGTTGCTGC  TGAAATCCTT  GGGATCAAAT  TAAACAANNA      720

GCAGAAWTRG  MACAGTCACA  GWGGGGTGGT  GAAGGSAGRT  ATTGTAAACT  ACAACCAGGA      780

ACCTATGTCA  AGGACTKTTA  ACCCTCCTAG  AAGCTCTATG  TGTGCAGTTC  AGTGAGCGCA      840

TTTTNCTTTT  GTNTTGATAG  TTCTGGCTGC  CCTTCAACTC  TGGGTGGGNC  CCNAGGGCTT      900

CTAGGACTTG  TTTT                                                            914
```

( 2 ) INFORMATION FOR SEQ ID NO:3:

( i ) SEQUENCE CHARACTERISTICS:
        ( A ) LENGTH: 217 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: Consensus
        ( B ) CLONE: Consensus ( x i ) SEQUENCE DESCRIPTION: SEQ ID NO:3:

```
Met  Arg  Xaa  Lys  Met  Gly  Asn  Gly  Thr  Glu  Glu  Asp  Tyr  Asn  Phe  Val
 1              5                        10                       15

Phe  Lys  Val  Val  Leu  Ile  Gly  Glu  Ser  Gly  Val  Gly  Lys  Thr  Asn  Leu
              20                        25                       30

Leu  Ser  Arg  Phe  Thr  Arg  Asn  Glu  Phe  Ser  His  Asp  Ser  Arg  Thr  Thr
              35                        40                       45

Ile  Gly  Val  Glu  Phe  Ser  Thr  Arg  Thr  Val  Met  Leu  Gly  Thr  Ala  Ala
         50                        55                       60

Val  Lys  Ala  Gln  Ile  Trp  Asp  Thr  Ala  Gly  Leu  Glu  Arg  Tyr  Arg  Ala
 65                       70                       75                       80

Ile  Thr  Ser  Ala  Tyr  Tyr  Arg  Gly  Ala  Val  Gly  Ala  Leu  Leu  Val  Phe
                   85                        90                       95

Asp  Leu  Thr  Lys  His  Gln  Thr  Tyr  Ala  Val  Val  Glu  Arg  Trp  Leu  Lys
              100                       105                      110

Glu  Leu  Tyr  Asp  His  Ala  Glu  Ala  Thr  Ile  Val  Val  Met  Leu  Val  Gly
              115                       120                      125

Asn  Lys  Ser  Asp  Leu  Ser  Gln  Gly  Arg  Glu  Val  Pro  Thr  Glu  Glu  Ala
              130                       135                      140

Arg  Met  Phe  Ala  Glu  Asn  Asn  Gly  Leu  Leu  Phe  Leu  Glu  Thr  Ser  Ala
 145                      150                      155                      160

Leu  Asp  Ser  Thr  Asn  Val  Glu  Leu  Ala  Phe  Glu  Thr  Val  Leu  Lys  Glu
                   165                       170                      175

Ile  Phe  Ala  Lys  Val  Ser  Lys  Gln  Arg  Gln  Asn  Ser  Ile  Arg  Thr  Asn
              180                       185                      190

Ala  Ile  Thr  Leu  Gly  Ser  Ala  Gln  Xaa  Gly  Gln  Glu  Pro  Gly  Pro  Gly
              195                       200                      205

Glu  Lys  Arg  Ala  Cys  Cys  Ile  Ser  Leu
              210                       215
```

( 2 ) INFORMATION FOR SEQ ID NO:4:

( i ) SEQUENCE CHARACTERISTICS:
    ( A ) LENGTH: 847 base pairs
    ( B ) TYPE: nucleic acid
    ( C ) STRANDEDNESS: single
    ( D ) TOPOLOGY: linear ( v i i ) IMMEDIATE SOURCE:
    ( A ) LIBRARY: Consensus
    ( B ) CLONE: Consensus ( x i ) SEQUENCE DESCRIPTION: SEQ ID NO:4:

```
GGCATTGAGC CAACACACAG ATTTGTCGCC TCTGTCCCCG AAGACACCTG CACCCTCCAT      60
GCGGANCAAG ATGGGGAATG GAACTGAGGA AGATTATAAC TTTGTCTTCA AGGTGGTGCT     120
GATCGGCGAA TCAGGTGTGG GGAAGACCAA TCTACTCTCC CGATTCACGC GCAATGAGTT     180
CAGCCACGAC AGCCGCACCA CCATCGGGGT TGAGTTCTCC ACCCGCACTG TGATGTTGGG     240
CACCGCTGCT GTCAAGGCTC AGATCTGGGA CACAGCTGGC CTGGAGCGGT ACCGAGCCAT     300
CACCTCGGCG TACTATCGTG GTGCAGTGGG GGCCCTCCTG GTGTTTGACC TAACCAAGCA     360
CCAGACCTAT GCTGTGGTGG AGCGATGGCT GAAGGAGCTC TATGACCATG CTGAAGCCAC     420
GATCGTCGTC ATGCTCGTGG GTAACAAAAG TGACCTCAGC CAGGGCCGGG AAGTGCCCAC     480
TGAGGAGGCC CGAATGTTCG CTGAAAACAA TGGACTGCTC TTCCTGGAGA CCTCAGCCCT     540
GGACTCTACC AATGTTGAGC TAGCCTTTGA GACTGTCCTG AAAGAAATCT TTGCGAAGGT     600
GTCCAAGCAG AGACAGAACA GCATCCGGAC CAATGCCATC ACTCTGGGCA GTGCCCAGGN     660
TGGACAGGAG CCTGGCCCTG GGGAGAAGAG GGCCTGTTGC ATCAGCCTCT GACCTTGGCC     720
AGCACCACCT GCCCCACTG GCTTTTGGT GCCCCTTGTC CCCACTTCAG CCCCAGGACC      780
TTTCCTTGCC CTTTGGTTCC AGATATCAGA CTGTTCCCTG TTCACAGCAC CCTCAGGGTC     840
TTAAGGT                                                              847
```

( 2 ) INFORMATION FOR SEQ ID NO:5:

( i ) SEQUENCE CHARACTERISTICS:
        ( A ) LENGTH: 201 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: Consensus
        ( B ) CLONE: Consensus ( x i ) SEQUENCE DESCRIPTION: SEQ ID NO:5:

```
Met Ala Gly Lys Ser Ser Leu Phe Lys Val Ile Leu Leu Gly Asp Gly
 1               5                  10                  15
Gly Val Gly Lys Ser Ser Leu Met Asn Arg Tyr Val Thr Asn Lys Phe
                20                  25                  30
Asp Thr Gln Leu Phe His Thr Ile Gly Val Glu Phe Leu Asn Lys Asp
            35                  40                  45
Leu Glu Val Asp Gly His Phe Val Thr Met Gln Ile Trp Asp Thr Ala
        50                  55                  60
Gly Gln Glu Arg Phe Arg Ser Leu Arg Thr Pro Phe Tyr Arg Gly Ser
65                  70                  75                  80
Asp Cys Cys Leu Leu Thr Phe Ser Val Asp Ser Gln Ser Phe Gln
                85                  90                  95
Asn Leu Ser Asn Trp Lys Lys Glu Phe Ile Tyr Tyr Ala Asp Val Lys
                100                 105                 110
Glu Pro Glu Ser Phe Pro Phe Val Ile Leu Gly Asn Lys Ile Asp Ile
            115                 120                 125
```

| Ser | Glu | Arg | Gln | Val | Ser | Thr | Glu | Glu | Ala | Gln | Ala | Trp | Cys | Arg | Asp |
| | 130 | | | | | 135 | | | | | 140 | | | | |
| Asn | Gly | Asp | Tyr | Pro | Tyr | Phe | Glu | Thr | Ser | Ala | Lys | Asp | Ala | Thr | Asn |
| 145 | | | | | 150 | | | | | 155 | | | | | 160 |
| Val | Ala | Ala | Ala | Phe | Glu | Glu | Ala | Val | Arg | Arg | Val | Leu | Ala | Thr | Glu |
| | | | | 165 | | | | | 170 | | | | | 175 | |
| Asp | Arg | Ser | Asp | His | Leu | Ile | Gln | Thr | Asp | Thr | Val | Asn | Leu | His | Arg |
| | | | 180 | | | | | 185 | | | | | 190 | | |
| Lys | Pro | Lys | Pro | Ser | Ser | Ser | Cys | Cys | | | | | | | |
| | | | 195 | | | | | 200 | | | | | | | |

( 2 ) INFORMATION FOR SEQ ID NO:6:

( i ) SEQUENCE CHARACTERISTICS:
       ( A ) LENGTH: 1175 base pairs
       ( B ) TYPE: nucleic acid
       ( C ) STRANDEDNESS: single
       ( D ) TOPOLOGY: linear ( v i i ) IMMEDIATE SOURCE:
       ( A ) LIBRARY: Consensus
       ( B ) CLONE: Consensus ( x i ) SEQUENCE DESCRIPTION: SEQ ID NO:6:

| | | | | | |
|---|---|---|---|---|---|
| CACTGTGATG | AAACACTTTT | CCCGTGTCGT | TTGAGTGCAT | CTTCTCAACA | ACCCTAGGAG | 60 |
| GGTTCTTGAA | GCTTTTGAGA | TTAACAATGG | CAGGAAAATC | ATCACTTTTT | AAAGTAATTC | 120 |
| TCCTTGGAGA | TGGTGGAGTT | GGGAAGAGTT | CACTTATGAA | CAGATATGTA | ACTAATAAGT | 180 |
| TTGATACCCA | GCTCTTCCAT | ACAATAGGTG | TGGAATTTTT | AAATAAAGAT | TTGGAAGTGG | 240 |
| ATGGACATTT | TGTTACCATG | CAGATTTGGG | ACACGGCAGG | TCAGGAGCGA | TTCCGAAGCC | 300 |
| TGAGGACACC | ATTTTACAGA | GGTTCTGACT | GCTGCCTGCT | TACTTTTAGT | GTCGATGATT | 360 |
| CACAAAGCTT | CCAGAACTTA | AGTAACTGGA | AGAAAGAATT | CATATATTAT | GCAGATGTGA | 420 |
| AAGAGCCTGA | GAGCTTTCCT | TTTGTGATTC | TGGGTAACAA | GATTGACATA | AGCGAACGGC | 480 |
| AGGTGTCTAC | AGAAGAAGCC | CAAGCTTGGT | GCAGGGACAA | CGGCGACTAT | CCTTATTTTG | 540 |
| AAACAAGTGC | AAAAGATGCC | ACAAATGTGG | CAGCAGCCTT | TGAGGAAGCG | GTTCGAAGAG | 600 |
| TTCTTGCTAC | CGAGGATAGG | TCAGATCATT | TGATTCAGAC | AGACACAGTC | AATCTTCACC | 660 |
| GAAAGCCCAA | GCCTAGCTCA | TCTTGCTGTT | GATTGTTAGA | TTGTTGATGC | ATTCTAACCA | 720 |
| ACTCACACAT | ATACACAAAA | TCAACATGGG | GATGGAGAAG | AGAATTAGCG | TTTGCAGCAG | 780 |
| TGTATCATCT | ACTAATAAAA | TTAAACTAAT | GTTGCTGCTT | CATTAGTTGG | TGGGAGAAGG | 840 |
| GACACATCCA | CTCTTGGAGG | AATATATTTA | CTCAATAATG | GCACCTTACA | TTTATAAATT | 900 |
| GTAACAGTTG | TCTAATAACG | TTTCTTTAAT | TTAAATATGT | AAGTTGCAGA | GCTAATAAAT | 960 |
| GAAATGACCA | AGACTTTAAT | TATAATAAAA | ATAAGAAACT | TGACTATTCT | AGAAGTTATA | 1020 |
| CTTGGATTTT | TTCCTGGGAA | AATGGAGAAC | TACTTTTTAT | ATGTGTATGT | TTTTATGCAA | 1080 |
| TTAGCATTGT | ATTCTTGGTT | CAGGGAAATA | CTTTCCTAAA | GCAATAATGT | TAGATATTAA | 1140 |
| AGATTAAAAT | CTAATGTAAA | AAAAAAAAA | AAAAA | | | 1175 |

( 2 ) INFORMATION FOR SEQ ID NO:7:

( i ) SEQUENCE CHARACTERISTICS:
       ( A ) LENGTH: 221 amino acids
       ( B ) TYPE: amino acid
       ( C ) STRANDEDNESS: single
       ( D ) TOPOLOGY: linear (v i i) IMMEDIATE SOURCE:
(A) LIBRARY: GenBank
(B) CLONE: 1154901

(x i) SEQUENCE DESCRIPTION: SEQ ID NO:7:

| Met | Ser | Asp | Ser | Glu | Glu | Glu | Ser | Gln | Asp | Arg | Gln | Leu | Lys | Ile | Val |
|---|---|---|---|---|---|---|---|---|---|---|---|---|---|---|---|
| 1 | | | | 5 | | | | | 10 | | | | | 15 | |

| Val | Leu | Gly | Asp | Gly | Thr | Ser | Gly | Lys | Thr | Ser | Leu | Ala | Thr | Cys | Phe |
|---|---|---|---|---|---|---|---|---|---|---|---|---|---|---|---|
| | | | 20 | | | | | 25 | | | | | 30 | | |

| Ala | Gln | Glu | Thr | Phe | Gly | Lys | Gln | Tyr | Lys | Gln | Thr | Ile | Gly | Leu | Asp |
| | | 35 | | | | | 40 | | | | | 45 | | | |

| Phe | Phe | Leu | Arg | Arg | Ile | Thr | Leu | Pro | Gly | Asn | Leu | Asn | Val | Thr | Leu |
| | 50 | | | | | 55 | | | | | 60 | | | | |

| Gln | Val | Trp | Asp | Ile | Gly | Gly | Gln | Thr | Ile | Gly | Gly | Lys | Met | Leu | Asp |
| 65 | | | | | 70 | | | | | 75 | | | | | 80 |

| Lys | Tyr | Ile | Tyr | Gly | Ala | Gln | Gly | Ile | Leu | Leu | Val | Tyr | Asp | Ile | Thr |
| | | | | 85 | | | | | 90 | | | | | 95 | |

| Asn | Tyr | Gln | Ser | Phe | Glu | Asn | Leu | Glu | Asp | Trp | Tyr | Ser | Val | Val | Lys |
| | | | 100 | | | | | 105 | | | | | 110 | | |

| Thr | Val | Ser | Glu | Glu | Ser | Glu | Thr | Gln | Pro | Leu | Val | Ala | Leu | Val | Gly |
| | | 115 | | | | | 120 | | | | | 125 | | | |

| Asn | Lys | Ile | Asp | Leu | Glu | His | Met | Arg | Thr | Val | Lys | Pro | Asp | Lys | His |
| | 130 | | | | | 135 | | | | | 140 | | | | |

| Leu | Arg | Phe | Cys | Gln | Glu | Asn | Gly | Phe | Ser | Ser | His | Phe | Val | Ser | Ala |
| 145 | | | | | 150 | | | | | 155 | | | | | 160 |

| Lys | Thr | Gly | Asp | Ser | Val | Phe | Leu | Cys | Phe | Gln | Lys | Val | Ala | Ala | Glu |
| | | | | 165 | | | | | 170 | | | | | 175 | |

| Ile | Leu | Gly | Ile | Lys | Leu | Asn | Lys | Ala | Glu | Ile | Glu | Gln | Ser | Gln | Arg |
| | | | 180 | | | | | 185 | | | | | 190 | | |

| Val | Val | Lys | Ala | Asp | Ile | Val | Asn | Tyr | Asn | Gln | Glu | Pro | Met | Ser | Arg |
| | | 195 | | | | | 200 | | | | | 205 | | | |

| Thr | Val | Asn | Pro | Pro | Arg | Ser | Ser | Met | Cys | Ala | Val | Gln |
| | | 210 | | | | | 215 | | | | | 220 |

(2) INFORMATION FOR SEQ ID NO:8:

(i) SEQUENCE CHARACTERISTICS:
(A) LENGTH: 213 amino acids
(B) TYPE: amino acid
(C) STRANDEDNESS: single
(D) TOPOLOGY: linear (v i i) IMMEDIATE SOURCE:
(A) LIBRARY: GenBank
(B) CLONE: 436001

(x i) SEQUENCE DESCRIPTION: SEQ ID NO:8:

| Met | Gly | Asn | Gly | Lys | Glu | Glu | Asp | Tyr | Asn | Phe | Val | Phe | Lys | Val | Val |
|---|---|---|---|---|---|---|---|---|---|---|---|---|---|---|---|
| 1 | | | | 5 | | | | | 10 | | | | | 15 | |

| Leu | Ile | Gly | Glu | Ser | Gly | Val | Gly | Lys | Thr | Asn | Leu | Leu | Ser | Arg | Phe |
| | | | 20 | | | | | 25 | | | | | 30 | | |

| Thr | Arg | Asn | Glu | Phe | Ser | His | Asp | Ser | Arg | Thr | Thr | Ile | Gly | Val | Glu |
| | | 35 | | | | | 40 | | | | | 45 | | | |

| Phe | Ser | Thr | Arg | Thr | Val | Leu | Leu | Gly | Thr | Ala | Ala | Val | Lys | Ala | Gln |
| | 50 | | | | | 55 | | | | | 60 | | | | |

| Ile | Trp | Asp | Thr | Ala | Gly | Leu | Glu | Arg | Tyr | Arg | Ala | Ile | Thr | Ser | Ala |
| 65 | | | | | 70 | | | | | 75 | | | | | 80 |

| Tyr | Tyr | Arg | Gly | Ala | Val | Gly | Ala | Leu | Leu | Val | Phe | Asp | Leu | Thr | Lys |
| | | | | 85 | | | | | 90 | | | | | 95 | |

```
His Gln Thr Tyr Ala Val Val Glu Arg Trp Leu Lys Glu Leu Tyr Asp
            100                 105                 110
His Ala Glu Ala Thr Ile Val Val Met Leu Val Gly Asn Lys Ser Asp
            115                 120                 125
Leu Ser Gln Ala Arg Glu Val Pro Thr Glu Glu Ala Arg Met Phe Ala
        130                 135                 140
Glu Asn Asn Gly Leu Leu Phe Leu Glu Thr Ser Ala Leu Asp Ser Thr
145                     150                 155                 160
Asn Val Glu Leu Ala Phe Glu Thr Val Leu Lys Glu Ile Phe Ala Lys
                165                 170                 175
Val Ser Lys Gln Ile Gln Asn Ser Pro Arg Ser Asn Ala Ile Ala Leu
            180                 185                 190
Gly Ser Ala Gln Ala Gly Gln Glu Pro Gly Pro Gly Gln Lys Arg Ala
            195                 200                 205
Cys Cys Ile Asn Leu
            210
```

(2) INFORMATION FOR SEQ ID NO:9:

(i) SEQUENCE CHARACTERISTICS:
        (A) LENGTH: 201 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 486830

(xi) SEQUENCE DESCRIPTION: SEQ ID NO:9:

```
Met Ala Gly Lys Ser Ser Leu Phe Lys Val Ile Leu Leu Gly Asp Gly
1               5                   10                  15
Gly Val Gly Lys Ser Ser Leu Met Asn Arg Tyr Val Thr Asn Lys Phe
            20                  25                  30
Asp Thr Gln Leu Phe His Thr Ile Gly Val Glu Phe Leu Asn Lys Asp
            35                  40                  45
Leu Glu Val Asp Gly His Phe Val Thr Met Gln Ile Trp Asp Thr Ala
    50                  55                  60
Gly Gln Glu Arg Phe Arg Ser Leu Arg Thr Pro Phe Tyr Arg Gly Ser
65                  70                  75                  80
Asp Cys Cys Leu Leu Thr Phe Ser Val Asp Ser Gln Ser Phe Gln
                85                  90                  95
Asn Leu Ser Asn Trp Lys Lys Glu Phe Ile Tyr Tyr Ala Asp Val Lys
            100                 105                 110
Glu Pro Glu Ser Phe Pro Phe Val Ile Leu Gly Asn Lys Ile Asp Ile
            115                 120                 125
Ser Glu Arg Gln Val Ser Thr Glu Glu Ala Gln Ala Trp Cys Arg Asp
        130                 135                 140
Asn Gly Asp Tyr Pro Tyr Phe Glu Thr Ser Ala Lys Asp Ala Thr Asn
145                     150                 155                 160
Val Ala Ala Ala Phe Glu Glu Ala Val Arg Arg Val Leu Ala Thr Glu
                165                 170                 175
Asp Arg Ser Asp His Leu Ile Gln Thr Asp Thr Val Ser Leu His Arg
            180                 185                 190
Lys Pro Lys Pro Ser Ser Ser Cys Cys
            195                 200
```